United States Patent [19]

Kolar et al.

[11] Patent Number: 5,049,549
[45] Date of Patent: Sep. 17, 1991

[54] RHODOMYCINS WITH A MODIFIED CARBOHYDRATE UNIT

[75] Inventors: Cenek Kolar; Hans P. Kraemer; Konrad Dehmel, all of Marburg, Fed. Rep. of Germany

[73] Assignee: Behringwerke Aktiengesellschaft, Marburg, Fed. Rep. of Germany

[21] Appl. No.: 451,877

[22] Filed: Dec. 18, 1989

[30] Foreign Application Priority Data

Dec. 20, 1988 [DE] Fed. Rep. of Germany ....... 3842836

[51] Int. Cl.$^5$ .................... C07H 15/252; A61K 31/71
[52] U.S. Cl. ...................... 514/34; 536/4.1; 536/6.4; 536/17.2; 536/18.1
[58] Field of Search ........................ 536/6.4, 4.1, 17.2, 536/18.1; 514/34

[56] References Cited

U.S. PATENT DOCUMENTS

| 4,316,011 | 2/1982 | Oki et al. | 536/6.4 |
| 4,366,149 | 12/1982 | Bargiotti et al. | 536/6.4 |
| 4,393,052 | 7/1983 | Bargiotti et al. | 536/6.4 |
| 4,439,603 | 3/1984 | Umezawa et al. | 536/6.4 |
| 4,684,629 | 8/1987 | Bargiotti et al. | 536/6.4 |
| 4,713,371 | 12/1987 | Aretz et al. | 536/6.4 |
| 4,948,880 | 8/1990 | Hermentin et al. | 536/6.4 |
| 4,987,126 | 1/1991 | Bargiotti et al. | 536/6.4 |

FOREIGN PATENT DOCUMENTS 0051279 5/1982 European Pat. Off. .
0199920 12/1986 European Pat. Off. .

OTHER PUBLICATIONS

Tanaka et al; Tetrahedron Letters 25(31):3355–3358 (1984).
C. Monneret et al., Anthracycline Antibiotics, 1982, pp. 225–251.
D. Horton et al., Anthracycline Antibiotics, 1982, pp. 197–224.

Primary Examiner—Ronald W. Griffin
Assistant Examiner—Nancy S. Carson
Attorney, Agent, or Firm—Finnegan, Henderson, Farabow, Garrett, and Dunner

[57] ABSTRACT

7-O-Glycosyl-rhodomycins which correspond to the general formula I below

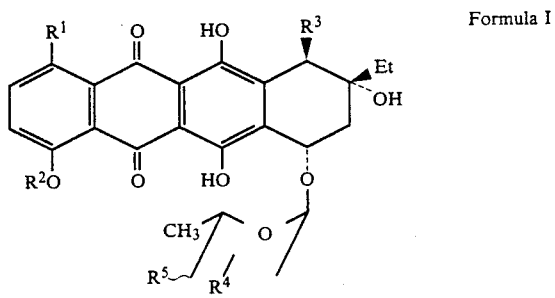

Formula I in which the radicals have the following meaning:

$R^1$ is a hydrogen atom or a hydroxyl group,
$R^2$ is a hydrogen atom or a $C_1$–$C_4$-alkyl group,
$R^3$ a hydroxyl group, an O-acyl protective group or the methyloxycarbonyl group,
$R^4$ is a hydrogen atom, an O-acyl protective group, an azido group, amino or trifluoroacetylamino group, a di-$C_1$–$C_4$-alkylamino group or cyanomethylamino group and
$R^5$ is an azido group, amino or trifluoroacetylamino group, a di-$C_1$–$C_4$-alkylamino group or cyanomethylamino group, where acyl protective group denotes an acetyl, mono-, di- or trihalogenoacetyl group with fluorine or chlorine as halogen or the p-nitrobenzoyl group, and a process for the preparation thereof and the use thereof as pharmaceuticals, are described.

7 Claims, No Drawings

RHODOMYCINS WITH A MODIFIED CARBOHYDRATE UNIT

The present invention relates to new anthracycline derivatives with cytostatic activity, and it specifically relates to 7-O-glycosyl-rhodomycins which are modified at the C-4' atom of the carbohydrate unit, to a process for the preparation thereof and to the use thereof as pharmaceuticals.

The anthracycline class of substances has been described in detail in the specialist literature. Doxorubicin and its 14-deoxy analog daunorubicin are mentioned as the most successful representatives of this class of substances and are employed clinically for the treatment of a large number of solid tumors and leukemias. However, the success of these specific compounds is not the same with all patients, and the success rate is lower with some specific types of tumors such as colon cancer and melanoma. Side effects of the treatment with doxorubicin and daunorubicin are, inter alia, damage to the circulatory system and symptoms characteristic thereof.

A number of other analogs which have been modified both in the aglycone moiety and in the carbohydrate unit have furthermore been described, especially those of the doxorubicin/daunorubicin type. In the case of rhodomycins, the derivatives which have been described contain a natural synthetic 3-aminosugar segment, but compounds modified at the C-4' atom of the carbohydrate unit have not hitherto been described.

Starting from this state of the art, the object of the present invention is to provide, starting from a rhodomycin aglycone and a C-4-modified functionalized carbohydrate, new rhodomycinone glycosides which are distinguished by a new spectrum of action and lower toxicity.

It has surprisingly emerged on glycosidation of 10-acyl-protected β-rhodomycinone with a 4-amino-daunosamine derivative that only alpha-O-glycosidically linked products are produced. The alpha-O-glycosidic linkage in the anthracyclines is essential for displaying the cytostatic activity thereof. The new derivatives were less cytotoxic than the known 7-O-(daunosaminyl)-β-rhodomycinone.

Based on these findings, the present invention has the additional object of, starting from rhodomycin aglycone and 4-amino- or azido-carbohydrate derivatives, preparing 7-O-glycosyl-rhodomycinones which have an improved spectrum of action and can be used as agents for tumor therapy.

This object is achieved with anthracycline derivatives which have cytostatic activity and correspond to the formula I

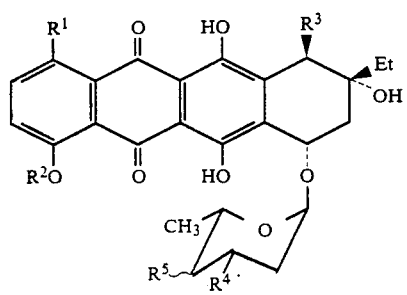
Formula I in which the radicals have the following meaning:
$R^1$ is a hydrogen atom or a hydroxyl group,
$R^2$ is a hydrogen atom or a $C_1$–$C_4$-group,
$R^3$ is a hydroxyl group, an O-acyl protective group or the methyloxycarbonyl group,
$R^4$ is a hydrogen atom, an O-acyl protective group, an azido group, an amino or trifluoroacetylamino group, a di-$C_1$–$C_4$-alkylamino group or cyanomethylamino group and
$R^5$ is an azido group, amino or trifluoroacetylamino group, a di-$C_1$–$C_4$-alkylamino group or cyanomethylamino group,
where acyl protective group denotes an acetyl, mono-, di- or trihalogenoacetyl group with fluorine or chlorine as halogen or the p-nitrobenzoyl group.

Preferred compounds of the formula I are those in which
$R^1$ is H or OH,
$R^2$ is H or $CH_3$,
$R^3$ is OH, $F_3CCOO$, p-$NO_2$-PhCOO or $COOCH_3$,
$R^4$ is H, OH, pNO$_2$-PhCOO, $N_3$, $NH_2$, $NHCOCF_3$, $N(CH_3)_2$ or $NHCH_2CN$ and
$R^5$ is $N_3$, $NH_2$, $NHCOCF_3$, $N(CH_3)_2$ or $NHCH_2$-CN.

The compounds of the formula I can, where appropriate, be in the form of ammonium salts.

The invention furthermore relates to a process for the preparation of one of the compounds of the formula I, which comprises
(a) reacting an aglycone compound of the formula II

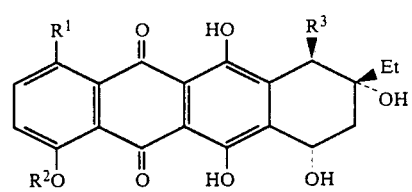
Formula II in which the radicals
$R^1$ is H or OH,
$R^2$ is H or $C_1$–$C_4$-alkyl and
$R^3$ is O-acyl protective group or $COOCH_3$,
with a functionalized deoxysugar of the formula III or IV

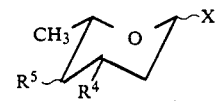
Formula III

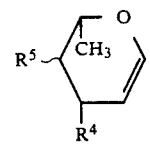
Formula IV in which the radicals
$R^4$ represents a hydrogen atom, an O-acyl protective group, azido group or trifluoroacetylamino group,
$R^5$ represents an azido group or a trifluoroacetylamino group and
X represents an acetyloxy, p-nitrobenzoyloxy group or a chlorine atom,
in the presence of a catalyst, preferably of a tri-$C_1$–$C_4$-alkylsilyl trifluoromethanesulfonate or the silver salt of trifluoromethanesulfonic acid, to give a 7-O-glycosyl-rhodomycinone derivative, and eliminating the acyl protective groups in the product partially or completely by alkaline hydrolysis, and converting the azido group present in the product, by hydrogenolysis in the presence of a hydrogenation catalyst such as palladium/carbon, into the amino group, resulting in a compound of the formula I in which the radicals $R^1$ and $R^2$ and remain unchanged, and $R^3$ represents OH or COOCH$_3$, $R^4$ represents a hydrogen atom, a hydroxyl group, an acetyloxy, trifluoroacetyloxy or p-nitrobenzoyloxy group or an azido, trifluoroacetylamino or amino group, and $R^5$ represents an azido group, an amino or trifluoroacetylamino group, (b) reacting a compound of the formula I, containing an aminosugar, from the first process step (a) in a manner known per se under the conditions of alkylation with a halogenoacetonitrile or of reductive alkylation with a C$_1$–C$_4$-aldehyde in the presence of an alkali metal cyanoborohydride to give another compound of the formula I in which the radicals $R^1$, $R^2$ and $R^3$ are unchanged, and $R^4$ represents a di-C$_1$–C$_4$-group or cyanomethylamino group and $R^5$ represents a di-C$_1$–C$_4$-alkylamino group or cyanomethylamino group.

The compounds of the formula I can, when appropriate, be converted into ammonium salts of pharmaceutically acceptable inorganic or organic acids. The following acids may be mentioned as representative in this connection: hydrochloric acid, glutamic acid and glucuronic acid.

The invention furthermore relates to the use of a compound of the formula I as a pharmaceutical.

The invention furthermore relates to pharmaceutical compositions which contain an anthracycline glycoside of the formula I or one of the pharmaceutically acceptable salts thereof together with a pharmaceutically acceptable diluent or excipient. These compositions contain a therapeutically effective amount of the anthracycline glycoside or of the salt thereof.

The invention furthermore relates to the use of the anthracycline glycosides of the formula I or of the salts thereof in a process for the preparation of an agent for treating certain mammalian tumors by administration of a therapeutically effective amount to a patient.

The cytostatic activity of the compounds described herein was determined in vitro on L1210 mouse leukemia cells or in vivo on L1210 leukemia, B-16 melanoma and Lewis lung adenocarcinoma. The acute toxicity of the compounds was determined in NMR1 mice. The methods and results of this investigation are described in the experimental part.

EXAMPLES

The structure of the compounds described in the following examples was established by NMR and MS analyses. The progress of the reactions and the chemical purity of the compounds was investigated by thin-layer chromatography or HPLC.

The following rhodomycinone aglycones were used as starting compounds for the preparation of the 7-O-glycosyl-rhodomycinone compounds according to the invention:

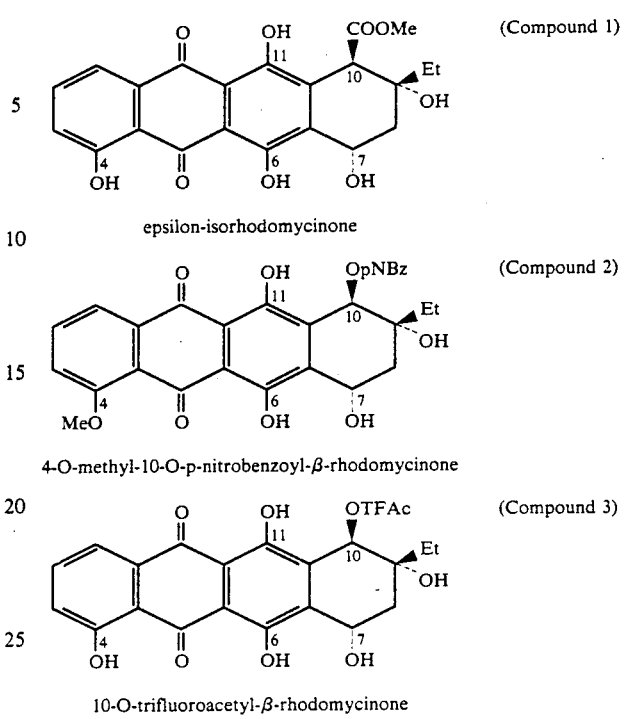

epsilon-isorhodomycinone (Compound 1)

4-O-methyl-10-O-p-nitrobenzoyl-β-rhodomycinone (Compound 2)

10-O-trifluoroacetyl-β-rhodomycinone (Compound 3)

The rhodomycinone aglycones were prepared by the process customary in anthracycline chemistry.

The functionalized carbohydrates used for glycosidation of the aglycones were prepared in analogy to the processes customary in carbohydrate chemistry. C. Monneret, J. Boivin, A. Martin and M. Pais in Anthracycline Antibiotics, Edit. H. S. El Khadem, 1982, pages 225-251 and D. Horton and W. Priebe, ibid., pages 197-224.

EXAMPLE 1

Preparation of epsilon-isorhodomycins (glycosidation and deblocking reactions)

7-O-(3'-O-p-Nitrobenzoyl-2',4',6'-trideoxy-4'-trifluoroacetamido-alpha-L-lyxohexopyranosyl)-epsilon-isorhodomycinone (compound 4)

200 mg (0.45 mmol) of compound 1 were dissolved in 40 ml of dichloromethane/acetone (10:1), and 680 mg (2.8 eq) of 1,3-O-bis-O-(p-nitrobenzoyl)-2,4,6-trideoxy-4-trifluoroacetamido-L-lyxohexopyranose and 400 mg of 4 Angstrom molecular sieves were added. The reaction mixture was cooled to −30° C. and, with exclusion of moisture, 0.35 ml ( (5 eq) of trimethylsilyl trifluoromethanesulphonate was added. The reaction mixture was subsequently stirred at −30° C. for 2 hours and then neutralized with 0.62 ml (10 eq) of triethylamine and filtered. The filtrate was washed three times with ice-water. The organic phase was dried over sodium sulfate and evaporated in vacuo. The resulting crude product (500 mg), of which a small portion was purified on a silica gel plate for the purpose of determining the structure, was employed in the following reaction.

7-O-(2',4',6'-Trideoxy-4'-trifluoroacetamido-alpha-L-lyxo-hexopyranosyl)-epsilon-isorhodomycinone (compound 5) 500 mg of compound 4 (crude product) were dissolved in 40 ml of chloroform/methanol and, at room temperature, 1 ml of 0.1 N aqueous NaOH solution was added. The reaction mixture was stirred for 2 hours and subsequently neutralized with 1 ml of 0.1 N aqueous hydrochloric acid. The mixture was subsequently washed three times with ice-water, back-extracting with dichloromethane. The organic phase was dried over sodium sulfate and evapoated in vacuo. The resulting residue was purifed by column chromatography (silica gel; dichloromethane/methanol 20:1).

Yield: 240 mg (79%)

7-O-(4'-Amino-2',4',6'-trideoxy-alpha-L-lyxohexopyrano- syl)-epsilon-isorhodomycinone (compound 5)

200 mg (0.298 mmol) of compound 5 were dissolved in 30 ml of chloroform/methanol, and 1 N aqueous NaOH solution was added. The reaction mixture was stirred at room temperature for 2 hours and then neutralized with 1 ml of aqueous hydrochloric acid and evaporated in vacuo. The residue was taken up in 25 ml of chloroform/methanol and . dried by stirring with sodium sulfate. The drying agent was filtered off and then the filtrate was evaporated. The residue was purified by column chromatography (silica gel; chloroform/methanol 5:1).

Yield: 130 mg (76%) MS; FAB m/e=574 (M+H+)

EXAMPLE 2

Preparation of 4-O-methyl-β-rhodomycins (glycosidation and deblocking reactions)

4-O-Methyl-10-O-p-nitrobenzoyl-7-O-(3'-O-p-nitrobenzoyl-2',4',6'-trideoxy-4'-trifluoroacetamido-alpha-L-lyxo-hexopyranosyl)-β-rhodomycinone (compound 6)

1.5 g (2.73 mmol) of compound 2 were dissolved in 300 ml of dichloromethane/acetone (10:1), and 2.95 g (2 eq) of 1,3-bis-O-(p-nitrobenzoyl)-2,4,6-trideoxy-4-trifluoroacetamido-L-lyohexopyranose and 3 g of 4 A molecular sieves were added. The reaction mixture was cooled to −30° C. and 2.1 ml (5 eq) of trimethylsilyl trifluoromethanesulfonate were added, and the mixture was stirred with exclusion of moisture for 1 hour. 3.7 ml (10 eq) of triethylamine were added to the reaction mixture, which was filtered. The filtrate was washed three times with water, dried over sodium sulfate and evaporated vacuo. The resulting crude product was purified by column chromatography (silica gel; dichloromethane/petroleum ether/ethyl acetate/acetone 70:25:2.5:2.5).

Yield: 1.74 g (70%)

(alpha)$_D$= +304° (c=0.05 in chloroform)

$^1$H-NMR and H,H-COSY (300 MHz, CDCl$_3$, delta): 7.94 (dd, J
=7.5 Hz and 1 Hz, H-1), 7.72 (t, J=7.5 Hz and 8 Hz, H-2), 7.34 (dd, J=8 Hz and 1 Hz, H-3), 5.27 (d, J= 4 Hz, H-7), 2.15 (dd, J=15 Hz and 4 Hz, H-8a), 2.38 (d,
J=15 Hz, H-8b), 6.53 (s, H-10), 1.83 (m, J=15 Hz and 7.4 Hz, H-13a), 1.48 (m, J=15 Hz and 7.4 Hz, H-13b), 1.04 (t, J=7.4 Hz, H-14), 13.87 and 13.74 (s, PhOH), 4.02 (s, OMe), 3.55 (s, 9-OH), 7.96-8.20 (m, p-NO2Ph),
5.62 (d, J=4.5 Hz, H-1'), 1.93 (td, J=3 Hz, 12.5 Hz and 4.5 Hz, H-2' ax), 2.21 (dd, J=13 Hz and 5.5 Hz, H-pb 2' eq), 5.32 (ddd, J=12.5 Hz, 5.5 Hz and 3.5 Hz, H-3'), 4.53 (d, J=8.5 Hz and 3.5 Hz, H-4'), 4.50 (q, J =6.5 Hz, H-5'), 1.25 (d, J=6.5 Hz, H-6'), 6.53 (d, J =8.5 Hz, N-H)

4-O-Methyl-7-O-(2',4',6'-trideoxy-4'-trifluoroacetamido-alpha-L-lyxohexo-pyranos-yl)-β-rhodomycinone (compound 7)

174 mg (0.19 mmol) of compound 6 were dissolved in 30 ml of chloroform/methanol and stirred with 1 ml of 1 N NaOH solution. After 30 min, the reaction was stopped by addition of 1 ml of 1 N hydrochloric acid. The reaction mixture was evaporated in vacuo and purified by column chromatography (silica gel; chloroform/methanol 5:1). Yield: 78 mg (66%)

(alpha)$_D$= +445° (c=0.1 in chloroform)

4-O-Methyl-7-O-(4'-amino-2',4',6'-trideoxy-alpha-L-lyxohexo-pyranosyl)-β-rhodomycinone (compound 8)

0.923 g (1 mmol) of compound 6 were dissolved in 150 ml of chloroform/methanol, and 12 ml of 1 N aqueous NaOH solution were added. The reaction mixture was stirred at room temperature for 3 hours and then neutralized with 12 ml of 1 N hydrochloric acid and evaporated in vacuo. The residue was dissolved in chloroform/methanl (5:1) and dried over sodium sulfate. The mixture was then filtered and the filtrate was evaporated in vacuo. The resulting crude product was purified by column chromatography on silica gel (mobile phase: chloroform/methanol/ammonia 65:35:1).

Yield: 396 mg (75%)

MS; FAB m/e=530 (M+H+) (alpha)$_D$= +41° (c=0.1 in chloroform)

$^1$H-NMR, H,H-COSY (300 MHz, CDCl$_3$/MeOD 5:1, delta): 7.82
(dd, J=7.5 Hz and 1 Hz, H-1), 7.64 (t, J=8 Hz and 7.5 Hz, H-2), 7.26 (dd, J=8 Hz and 1 Hz, H-3), 4.98 (br.s, J=3.8 Hz and 2 Hz, H-7), 2.11 (d, J=15 Hz and 2 Hz, H-8a), 2.04 (dd, J=15 Hz and 3.8 Hz, H-8b), 4.74
(s, H-10), 1.76 (m, J=15 Hz and 7.5 Hz, H-13a), 1.69 (m, J=15 Hz and 7.5 Hz, H-13b), 1.01 (t, J=7.5 Hz, H-14), 3.95 (s, OMe), 5.35 (d, J=3.7 Hz, H-1'), 1.61 (ddd, J=13 Hz, 13 Hz and 3.7 Hz, H-2ax), 1.78 (dd, J=
13 Hz and 4.0 Hz, H-2, eq), 3.77 (m, J=13 Hz, 4.0 Hz and 3.5 Hz, H-3'), 2.82 (d, J=3.5 Hz, H-4'), 4.12 (q, J=6.5 Hz, H-5'), 1.23 (d, J=6.5 Hz, H-6')

4-O-Methyl-10-O-p-nitrobenzoyl-7-O-(2',3',4',6'-tetradeoxy-3',4'-bis-(trifluoroacetamido)-alpha-L-lyxohexo-pyranosyl)-β-rhodomycinone (compound 9)

1 g (1.82 mmol) of compound 2 were dissolved in 200 ml of dichloromethane/acetone (10:1) and, while stirring, 2.21 g (2.5 eq) of 3,4-bis-(trifluoroacetamido)-1-O-p-nitrobenzoyl-2,3,4,6-tetradeoxy-alpha-β-L-lyxohexopyranose and 2 g of 4 A molecular sieves were added. The suspension was cooled to −30° C. and 1.4 ml (5 eq) of trimethylsilyl trifluoromethanesulphonate were added. The reaction mixture was stirred at −30° C. for 2 hours and then 2.5 ml (10 eq) of triethylamine were added, and the mixture was subsequently filtered. The filtrate was washed three times with water and then dried over sodium sulfate and evaporated in vacuo. The resulting product was purified by column chromatography on silica gel (eluent: dichloromethane/acetone 15:1).

Yield: 1.34 g (85%); melting point: 220-223° C.

(alpha)$_D$= +406° (c=0.5 in chloroform)

4-O-Methyl-7-O-(3',4'-diamino-2',3',4',6'-tetradeoxy-alpha-L-lyxohexopyranosyl)-β-rhodomycinone (compound 10)

1.34 g (1.54 mmol) of compound 9 were dissolved in 200 ml of chloroform/methanol and, at room temperature, 60 ml of 1 N NaOH were added. After 3 hours, the reaction mixture was neutralized with 60 ml of 1 N HCl and evaporated in vacuo. The residue was dissolved in chloroform/methanol (5:1), sodium sulfate was added and the suspension was then stirred for 20 min. It was filtered and evaporated in vacuo. The residue was purified by column chromatography on silica gel (eluent: chloroform/methanol/ammonia 65:35:1).

Yield: 0.63 g (77%)

MS: FAB, m/e=529 (M+H+) (alpha)$_D$=+355° (c=0.2 in methanol)

$^1$H-NMR, H,H-COSY (300 MHz, MeOD, delta): 7.50 (dd, J=
7.5 Hz and 1 Hz, H-1), 7.44 (t, J=8.5 Hz and 7.5 Hz, H-2), 7.15 (dd, J=8.5 Hz and 1 Hz, H-3), 4.93 (dd, J=4 Hz and 1.5 Hz, H-7), 2.06 (dd, J=15 Hz and 4 Hz, H-8a), 2.14 (dd, J=15 Hz and 1.5 Hz, H-8b), 4.68 (s, H-10), 1.68 (m, J=15 Hz and 7.5 Hz, H-13a), 1.74 (m, J
=15 Hz and 7.5 Hz, H-13b), 1.06 (t, J=7.5 Hz, H-14), 3.78 (s, OMe), 5.32 (d, J=3 Hz, H-1'), 1.64 (ddd, J=13 Hz, 13 Hz and H-2' ax), 1.76 (dd, J=13 Hz and 4 Hz,
H-2' eq), 3.06 (t, J=13 Hz, 4 Hz and 3 Hz, H-3'), 2.66 (d, J=3 Hz, H-4'), 4.22 (q, J=6.5 Hz, H-5'), 1.22 (d, J=6.5 Hz, H-6')

EXAMPLE 3

Preparation of β-rhodomycins (glycosidylation and deblocking reactions)

7-O-(3',4'-bis-(Trifluoroacetamido)-2',3',4',6'-tetradeoxy-alpha-L-arabinohexopyranosyl)-10-O-trifluoroacetyl-β-rhodomycinone (compound 11)

100 mg (0.203 mmol) of compound 3 were taken up in 20 ml of dichloromethane/acetone (10:1), and 197 mg (2 eq) of 3,4-bis-(trifluoroacetamido)-1-O-p-nitrobenzoyl-2,3,4,6-tetradeoxy-alpha,β-L-arabinohexopyranose and 200 mg of 4 A molecular sieves were added. The reaction mixture was cooled to −30° C., 0.1 ml (3 eq) of trimethylsilyl trifluoromethanesulfonate was added and the mixture was stirred for 2 hours. The reaction mixture was neutralized with 0.1 ml of triethylamine and filtered. The filtrate was stirred with sodium sulfate, filtered and evaporated in vacuo. The crude product was purified by column chromatography under silica gel (eluent: dichloromethane/acetone 15:1).

Yield: 125 mg (76.6%)

7-O-(3'-Amino-2',3',4',6'-tetradeoxy-4'-trifluoroacetamido-alpha-L-arabinohexopyranosyl)-β-rhodomycinone (compound 12)

125 mg (0.155 mmol) of compound 11 were dissolved in 10 ml of chloroform/methanol, and 2 ml of 1 N NaOH were added. After 2 hours, the reaction mixture was neutralized with 1 N HCl and filtered. The filtrate was evaporated in vacuo. The residue was distilled in chloroform/methanol, dried over sodium sulfate and purified by column chromatography on silica gel (eluent: chloroform/methanol/water 4:4:1).

Yield: 72 mg (0.76%)

MS: FAB m/e=611 (M+H+)

The structure of the compound was elucidated by using $^1$H 300 MHz NMR and H,H-COSY, especially the presence of the 4'-trifluoroacetamido group.

7-O-(3'-Azido-2',3',4',6'-tetradeoxy-4'-trifluoroacetamido-alpha-L-lyxohexopyranosyl)-β-rhodomycinone (compound 13)

115 mg (0.238 mmol) of compound 3 were taken up in 20 ml of dichloromethane/acetone 10:1, and 300 mg (3 eq) of 3-azido-1-O-p-nitrobenzoyl-2,3,4,6-tetradeoxy-4-trfluoroacetamido-alpha,-L-lyxohexopyranose and 250 mg of 4 A molecular sieves were added. The reaction mixture was cooled to −50° C. and 264 mg (5 eq) of trimethylsilyl trifluoromethanesulfonate were added. After 2 hours, the reaction mixture was neutralized with 0.16 ml (5 eq) of triethylamine and filtered. The filtrate was mixed with a little n-butanol, washed with 0.05 N NaOH, dried over sodium sulfate and evaporated in vacuo. The residue was purified by column chromatography on silica gel (eluent: dichloromethane/petroleum ether/acetone 5:5:1).

Yield: 110 mg (72%)

MS: FAB m/e=637 (M+H+)

$^1$H-NMR (270 MHz, CDCl$_3$/MeOD 3:1, delta): 7.82 (dd, H-1),
7.67 (t, H-2), 7.27 (dd, H-3), 5.05 (br.s, H-7), 2.13 (dd, H-8a), 2.07 (dd, H-8b), 5.79 (s, H-10), 1.69 (m, H-13a), 1.76 (m, H-13b), 1.03 (t, H-14), 5.44 (br. s, H-1'), 1.83 (ddd, H-2' ax), 1.94 (dd, H-2, eq), 3.83 (m, H-3'), 4.27 (br.d, H-4'), 4.29 (m, H-5'), 1.15 (d, H-6')

7-O-(3',4'-bis-(Trifluoroacetamido)-2',3',4',6'-tetradeoxy-alpha-L-lyxohexopyranosyl)-10-O-trifluoroacetyl-β-rhodomycinone (compound 14) and 7-O-(3',4'-bis-(trifluoroacetamido)-2',3',4',6'-tetradeoxy-alpha-L-lyxohexopyranosyl)-β-rhodomycinone (compound 15)

100 mg (0.207 mmol) of compound 3 were dissolved in 20 ml of dichloromethane/acetone 10:1, and 201 mg (2 eq) of 3,4-bis-(trifluoroacetamido-1-O-p-nitrobenzoyl-2,3,4,6-tetradeoxy-alpha,-L-lyxohexopyranose and 200 mg of molecular sieves were added. The reaction mixture was cooled to −30° C. and, with exclusion of moisture, 0.1 ml (3 eq) of trimethylsilyl triflate was added. After 2 hours, 0.1 ml of triethylamine was added to the reaction mixture, which was filtered. The filtrate was evaporated in vacuo, and the resulting crude product, which contained the compound 14, was employed without further purification in the next reaction stage. The crude product was dissolved in 10 ml of chloroform/methanol (3:1), and 1 ml of 0.1 N NaOH was added. The partial deblocking was complete after a reaction time of 10 min. The reaction mixture was neutralized with 1 ml of 0.1 N HCl and evaporated in vacuo. The residue was purified by column chromatography on silica gel (eluent: dichloromethane/acetone 10:1).

Yield: 100 mg (83.7%) of compound 15

MS: FAB, m/e=707 (M+H+); m/e=729 (M+Na+)

7-O-(3',4'-Diamino-2',3',4',6'-tetradeoxy-alpha-L-lyxohexo-pyranosyl)-β-rhodomycinone (compound 16)

100 mg (0.14 mmol) of compound 15 were dissolved in 10 ml of chloroform/methanol 3:1, and 2 ml of 1 N NaOH were added. The reaction mixture was stirred for 2 hours and then neutralized with 2 ml of 1 N HCl and evaporated in vacuo. The crude product was dried as usual over sodium sulfate and purified by column chromatography on silica gel (eluent: chloroform/methanol/water 4:4:1).

Yield: 58 mg (80.8%)

MS: FAB m/e=515 (M+H+)

7-O-(4'-Azido-2',3',4',6'-tetradeoxy-3'-trifluoroacetamido-alpha-L-arabinohexopyranosyl)-β-rhodomycinone (compound 17)

1 g (2.07 mmol) of compound 3 were dissolved in 150 ml of dichloromethane/acetone (10:1), and 2.6 g (3 eq) of 4-azido-1-O-p-nitrobenzoyl-2',3',4',6'-tetradeoxy-3-trifluoroacetamido-alpha-β-L-arabinohexopyranose and 2 g of 4 A molecular sieves were added. The reaction mixture was cooled to −30° C. and, under protective gas, 1.6 ml (5 eq) of trimethylsilyl triflate were added. The reaction mixture was stirred for 2 hours, then stirred with 1.4 ml (5 eq) of triethylamine and filtered. The fltrate was washed with 0.01 N NaOH and then with water and evaporated in vacuo. The residue was purified by column chromatography on silica gel (eluent: dichloromethane/acetone 10:1).

Yield: 0.94 g (72%)

7-O-(3'-O-p-Nitrobenzoyl-2',4',6'-trideoxy-4'-trifluoroacetamido-alpha-L-lyxohexopyranosyl)-10-O-trfluoroacetyl-β-rhodomycinone (compound 18)

500 mg (1.03 mmol) of compound 3 were dissolved in 90 ml of dichloromethane/acetone 10:1, and 1.4 g (2.5 eq) of 1,3-bis-(p-nitrobenzoyl)-2,4,6-trideoxy-4-trifluoroacetamido-alpha,-L-lyxohexopyranose and 1 g of 4 A molecular sieves were added. The reaction mixture was cooled to −30° C. and 1.1 g (5 eq) of trimethylsilyl triflate were added. The reaction mixture was stirred for 2 hours under protective gas and then 0.7 ml (5 eq) of triethylamine were added, and the mixture was filtered and evaporated in vacuo. The crude product was purified by column chromatography on silica gel (eluent: dichloromethane/petroleum ether/acetone 5:5:1).

Yield: 0.85 g (95%)

7-O-(4'-Amino-2',4',6'-trideoxy-alpha-L-lyxohexopyranosyl)-β-rhodomycinone (compound 19)

0.85 g (0.99 mmol) of compound 18 was dissolved in 100 ml of chloroform/methanol, and 10 ml of 1 N NaOH were added. After 2 hours, the reaction mixture was neutralized with 10 ml of 1 N HCl and evaporated in vacuo. The residue was dissolved in chloroform/methanol, stirred with sodium sulfate and filtered. The filtrate was evaporated in vacuo, and the resulting crude product was purified by column chromatography on silica gel (eluent: chloroform/methanol/ammonia 65:35:1).

Yield: 0.324 g (62%)

MS: FAB m/e=516 (M+H+)

EXAMPLE 4

Cytotoxicity for L1210 leukemia cells (stem cell assay)

Experimental procedure

The test was carried out in accordance with the methods described by Hamburger and Salmon, with the modifications described below.

Conditioned medium was replaced by McCoy 5A medium. As a consequence of the high cloning rate of the L1210 leukemia cells in soft agar, the number of tumor cells per plate was reduced to $5 \times 10^2$.

The cells were incubated with various concentrations of the test substance at 37° C. for 1 h. The cells were subsequently washed twice with McCoy 5A medium and subsequently plated out in a two-layer agar system as upper layer in accordance with the Hamburger and Salmon method.

Additional parallel experiments were carried out using a continuous incubation time, in which case various concentrations of the test substance were mixed with the upper agar layer before plating out of the cells.

The plates were incubated in an incubator with 5% $CO_2$, 20% $O_2$ and 95% relative humidity for 5–7 days. After this time, colonies with a diameter of 60 μm were counted using an invertoscope.

The results have been reported as the percentage of colonies in treated versus untreated groups. The coefficient of variation for repeat experiments was less than 15%.

Results

The tested compounds are contained in Table 1.

The $IC_{50}$ for continuous and one-hour incubation was determined from the dose-effect plot (Tab. 1).

Discussion

The numbers compiled in the Table demonstrate that most substances have a very high cytotoxicity ($IC_{50}$ less than 0.1 μg/ml) for human and animal tumor cells in various in vitro test systems.

EXAMPLE 5

Proliferation test (MTT reduction)

L1210, A 549 or HT 29 in the exponential growth phase are incubated in a cell density of $5 \times 10^3$ cells/ml in RPMI 1640 medium in a 96-well microtest plate with various concentrations of the test substance at 37° C., 5% $CO_2$ and 95% relative humidity for 72 h. Control experiments contain merely growth medium in place of test substance. Determinations in quadruplicate are made up for each test substance and for the control. After incubation for 65 h, 50 μl of an MTT solution (2.5 mg/ml in phosphate-buffered saline) are added. In the presence of live cells MTT is reduced to a dark-red insoluble formazan dyestuff. This reaction is complete after 7 h (L1210 cells) or after 24 h (A 549, HT 29 cells), and the supernatant medium is carefully aspirated off. The insoluble dyestuff is dissolved by addition of 100 μl of DMSO, and the extinction of the solution produced in this way is subsequently measured at a wavelength of 492 nm for each well in a 340 CC Multiscan Photometer from Flow.

The ratio of the extinctions with treated and untreated cells yields a dose-effect plot from which the concentration which just kills 50% of the cells ($IC_{50}$) can be read off. The coefficient of variation for repeat tests is less than 15%.

EXAMPLE 6

Determination of the acute toxicity

To determine the acute toxicity, BDF1 mice receive intraperitoneal injections of various doses of the test substance, dissolved in 0.5 ml of 5% strength glucose solution, on day 0. Control groups receive merely 0.5 ml of 5% strength glucose solution. 5 mice are used for each concentration of the test substance. On day 14, the number of surviving mice is determined and, from this, the LD5, LD50 and LD95 are determined by the Litchfield-Wilcoxon method. The toxicity (LD50 mg/kg) of the compounds described here was determined by comparison with adriamycin.

EXAMPLE 7

In vivo activity of the rhodomycins against L1210 leukemia in the mouse

Method

Ascites fluid is taken under sterile conditions from DBA2 mice (female, 18–20 g) 7 days after implantation. The ascites is washed three times with PBS, counted, and adjusted to a cell count of $10^5$ in 0.2 ml of PBS.

$10^5$ cells suspended in 0.2 ml of PBS are subsequently injected intraperitoneally into DBF1 mice (female, 18–20 g). 6 animals per group are employed for each substance concentration and as control.

Determination of the antitumor activity (a) The animals are weighed on days 1 and 5 after injection of the test substance. A weight loss of more than 20% on day 5 is regarded as an indicator of the toxic effect of the substance.

(b) At the end of the experiment (death of all animals, or animals surviving on day 60), the mean survival time of the animals in the particular groups is determined as long as at least 65% of the animals were still alive on day 5 of the experiment. The mean survival time is determined exclusively for animals dying during the course of the experiment. Long-term survivors (LTS) are not included in this calculation and are detailed separately.

The antitumor activity (T/C) for the particular substance concentration as a percentage of the untreated control is determined from the mean survival time ($MST_T$) of the treated groups and that of the control group ($MST_c$) using the following formula:

$$T/C\ \% = \frac{MST_T}{MST_c} \times 100$$

T/C values greater than 125% are regarded as an indicator of a significant antitumor activity of the test substance. The dose having the greatest antitumor effect (optimal dosage), as well as one dose level above and below this dose in each case, were determined. Animals still alive on day 60 of the experiment are listed separately as long-term survivors.

TABLE 1

| Compound No. | IC$_{50}$ (μg/ml) in vitro | | | | | L1210 LD$_{50}$ in vivo |
|---|---|---|---|---|---|---|
| | SCA cont. | 1 h | L1210 | A549 | HT29 | |
| 8 | | | 0.043 | 0.14 | 0.043 | |
| 10 | | | 0.039 | 0.095 | 0.033 | |
| 12 | | 0.44 | 0.03 | 0.027 | 0.022 | |
| 13 | | 0.29 | 0.10 | 0.10 | 0.20 | |
| 15 | | 0.43 | 0.037 | 0.059 | 0.10 | |
| 16 | | 0.069 | 0.01 | 0.04 | 0.069 | |
| 17 | | 1.4 | 0.33 | 0.52 | 0.34 | |
| Adriamycin | 0.02 | 0.04 | | | | |

We claim:

1. A compound of the formula I

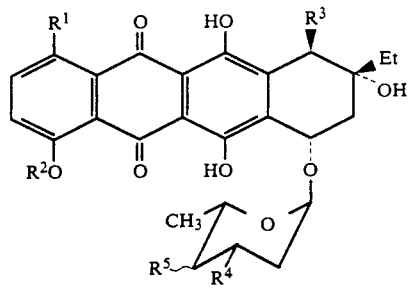

Formula I in which the radicals have the following meaning:
$R^1$ is a hydrogen atom or a hydroxyl group,
$R^2$ is a hydrogen atom or a $C_1$–$C_4$-group,
$R^3$ is a hydroxyl group, an O-acyl protective group or a methyloxycarbonyl group,
$R^4$ is a hydrogen atom, an O-acyl protective group, an azido group, an amino or trifluoroacetylamino group, a di-$C_1$–$C_4$-alkylamino group or cyanomethylamino group and
$R^5$ is an azido group, amino or trifluoroacetylamino group, a di-$C_1$–$C_4$- alkylamino group or cyanomethylamino group, where acyl protective group denotes an acetyl, mono-, di- or trihalogenoacetyl group with fluorine or chlorine as halogen or a p-nitrobenzoyl group, and the salts thereof.

2. A compound as claimed in claim 1, in which
$R^1$ is H or OH,
$R^2$ is H or $CH_3$,
$R^3$ is OH, $F_3CCOO$, p-$NO_2$-PhCOO or $COOCH_3$,
$R^4$ is H, OH, p$NO_2$-PhCOO, $N_3$, $NH_2$, $NHCOCF_3$, $N(CH_3)_2$ or $NHCH_2CN$ and
$R^5$ is $N_3$, $NH_3$, $NHCOCF_3$, $N(CH_3)_2$ or $NHCH_2$-CN.

3. A compound as claimed in claim 1, in which the radicals $R^1$, $R^2$, $R^4$ and $R^5$ have the meaning specified in claim 1, and $R^3$ is a methyloxycarbonyl group.

4. A compound as claimed in claim in which the radicals $R^1$, $R^2$, $R^4$ and $R^5$ have the meaning specified in claim 1, and $R^3$ is a hydroxyl group.

5. A compound as claimed in claim 1, in which
$R^1$ is H or OH and
$R^2$ is a $C_1$–$C_4$-alkyl group, and
the radicals $R^3$, $R^4$ and $R^5$ have the meaning specified in claim 1.

6. A pharmaceutical composition containing a therapeutically effective amount of a compound as claimed in claim 1 together with a pharmaceutically acceptable carrier.

7. A process for the preparation of a compound as claimed in claim 1, which comprises reacting an aglycone compound of the formula II

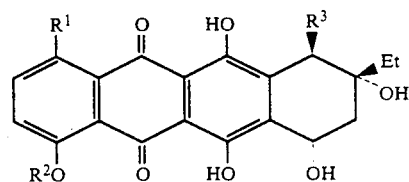

Formula II in which the radicals
$R_1$ is H or OH,
$R^2$ is H or $C_1$–$C_4$-alkyl and
$R^3$ is O-acyl group or $COOCH_3$, with a functionalized deoxysugar of the formula III or IV

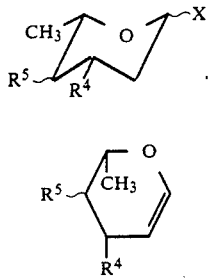
Formula III

Formula IV in which the radicals

R⁴ represents a hydrogen atom, an O-acyl protective group, azido group or trifluoroacetylamino group, R⁵ represents an azido group or a trifluoroacetylamino group and X represents an acetyloxy, p-nitrobenzoyloxy group or a chlorine atom, in the presence of a catalyst, selected from the group consisting of tri-$C_1$–$C_4$-alkylsilyl trifluoromethanesulfonate or the silver salt of trifluoromethanesulfonic acid, to give a 7-O-glycosyl-rhodomycinone derivative, and eliminating the acyl protective groups in the product partially or completely by alkaline hydrolysis, and converting the azido group present in the product, by hydrogenolysis in the presence of a hydrogenation catalyst such as palladium/carbon, into the amino group, resulting in a compound of the formula I in which the radicals R¹ and R² remain unchanged, and R³ represents OH or COOCH₃, R⁴ represents a hydrogen atom, a hydroxyl group, an acetyloxy, trifluoroacetyloxy or p-nitrobenzoyloxy group or an azido, trifluoroacetylamino or amino group, and R⁵ represents an azido group, an amino or trifluoroacetylamino group.

* * * * *